(12) United States Patent
Fan et al.

(10) Patent No.: US 10,441,748 B2
(45) Date of Patent: Oct. 15, 2019

(54) FLEXIBLE AND/OR PUSHABLE TUBULAR DEVICE

(71) Applicant: GYRUS ACMI, INC., Southborough, MA (US)

(72) Inventors: Tailin Fan, Nashua, NH (US); Jane Bareau, Needham, MA (US)

(73) Assignee: GYRUS ACMI, INC., Southborough, MA (US)

( * ) Notice: Subject to any disclaimer, the term of this patent is extended or adjusted under 35 U.S.C. 154(b) by 457 days.

(21) Appl. No.: 15/155,697

(22) Filed: May 16, 2016

(65) Prior Publication Data

US 2017/0326335 A1    Nov. 16, 2017

(51) Int. Cl.
| | | |
|---|---|---|
| *A61M 25/00* | (2006.01) | |
| *B29D 23/00* | (2006.01) | |
| *A61M 25/01* | (2006.01) | |
| *B33Y 80/00* | (2015.01) | |

(52) U.S. Cl.
CPC .... *A61M 25/0138* (2013.01); *A61M 25/0054* (2013.01); *B33Y 80/00* (2014.12); *A61M 25/0147* (2013.01); *B29D 23/00* (2013.01)

(58) Field of Classification Search
CPC .......... A61M 25/0054; A61M 25/0138; A61M 25/0147; A61M 25/0012; A61M 25/0141; A61M 25/0144; A61M 25/0152; A61M 25/005; A61M 25/0051; A61M 25/0052; A61M 25/0053

See application file for complete search history.

(56) References Cited

U.S. PATENT DOCUMENTS

| | | | | | |
|---|---|---|---|---|---|
| 5,152,744 | A | * | 10/1992 | Krause | A61B 17/32002 604/22 |
| 5,947,940 | A | * | 9/1999 | Beisel | A61M 25/005 604/264 |
| 6,159,187 | A | * | 12/2000 | Park | A61L 29/14 604/264 |
| 6,217,566 | B1 | * | 4/2001 | Ju | A61M 25/005 604/526 |
| 8,323,241 | B2 | * | 12/2012 | Salahieh | A61M 25/0136 604/95.04 |
| 8,721,826 | B2 | | 5/2014 | Hart et al. | |
| 9,233,225 | B2 | * | 1/2016 | Hebert | A61M 25/0138 |
| 2005/0075538 | A1 | * | 4/2005 | Banik | A61B 1/00071 600/141 |

(Continued)

FOREIGN PATENT DOCUMENTS

| | | |
|---|---|---|
| WO | 2010/105649 A1 | 9/2010 |
| WO | 2014/074986 A1 | 5/2014 |

*Primary Examiner* — Jenna Zhang
(74) *Attorney, Agent, or Firm* — The Dobrusin Law Firm, P.C.

(57) ABSTRACT

The teachings herein relate to devices for insertion into a cavity, opening or other passageway that requires the bending of the device to conform to a curved or even tortuous shape of the path. The devices include axial support components for translating forces for moving the device forward in the path. The axial support components preferably include adjacent components capable of rocking for tilting the device in one or more directions. The device preferably includes one or more lateral support components for limiting any lateral motion of an axial support component relative to an adjacent axial support component.

17 Claims, 9 Drawing Sheets

(56) References Cited

U.S. PATENT DOCUMENTS

| | | | | |
|---|---|---|---|---|
| 2007/0219465 | A1* | 9/2007 | Cedro | A61M 25/0138 600/585 |
| 2008/0172037 | A1* | 7/2008 | Huang | A61M 25/0043 604/526 |
| 2008/0287741 | A1* | 11/2008 | Ostrovsky | A61B 1/00071 600/141 |
| 2009/0105816 | A1* | 4/2009 | Olsen | A61B 17/00234 623/2.37 |
| 2010/0331618 | A1* | 12/2010 | Galperin | A61B 1/00071 600/101 |
| 2011/0066105 | A1* | 3/2011 | Hart | A61B 17/3421 604/95.04 |
| 2011/0264011 | A1* | 10/2011 | Wu | A61B 18/082 601/2 |
| 2012/0277730 | A1* | 11/2012 | Salahieh | A61B 1/00135 604/527 |
| 2014/0135736 | A1* | 5/2014 | Hebert | A61M 25/0138 604/525 |
| 2018/0304040 | A1* | 10/2018 | Jalgaonkar | A61M 25/0051 |

* cited by examiner

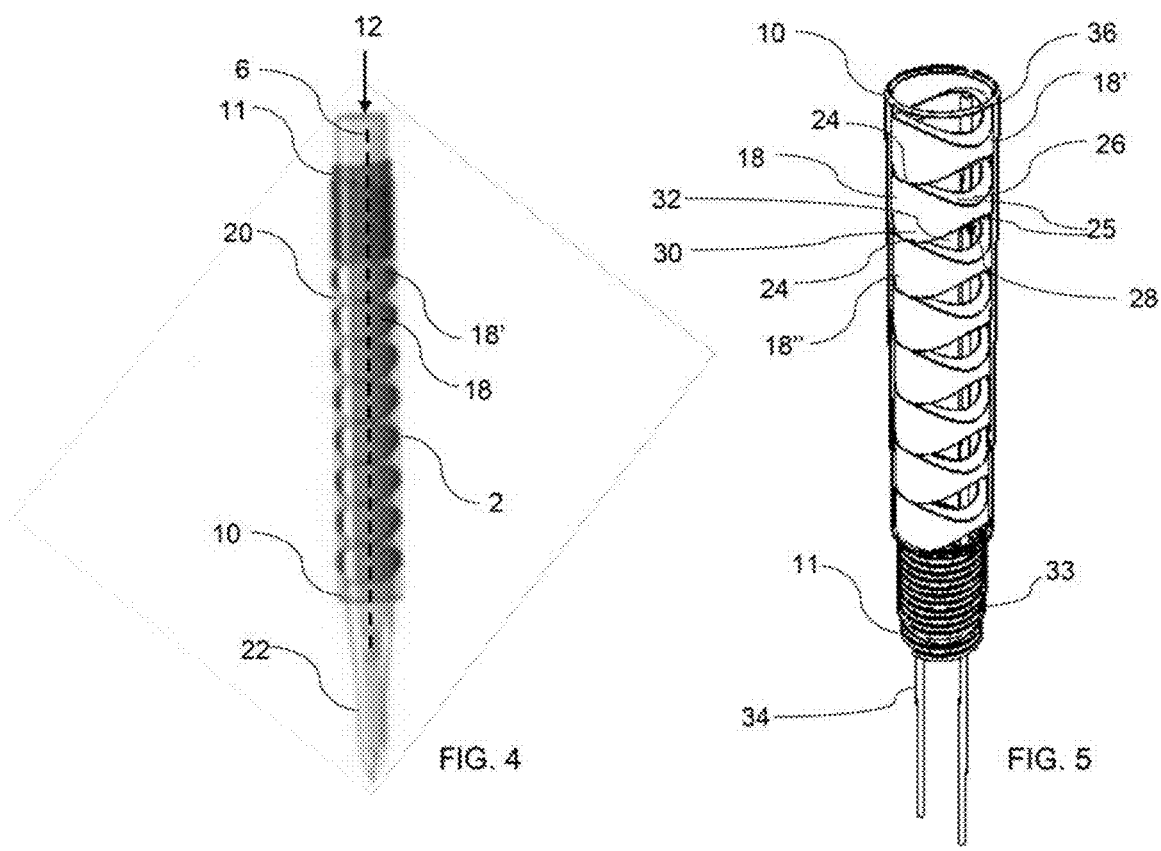

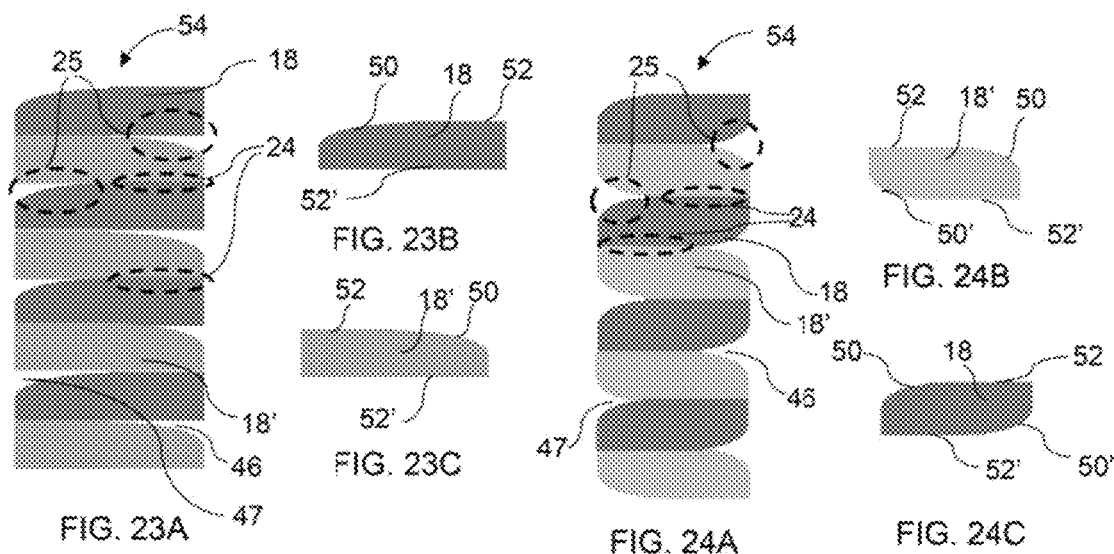
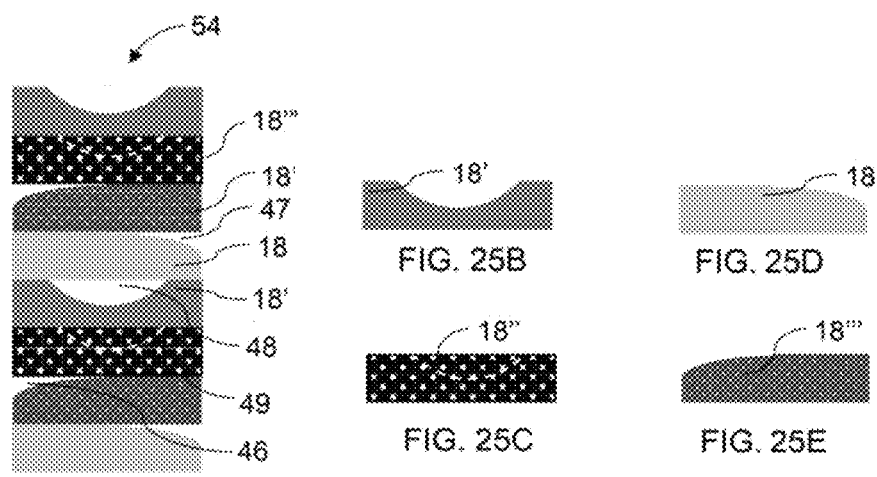

FLEXIBLE AND/OR PUSHABLE TUBULAR DEVICE

FIELD

The teachings herein are directed at methods and devices including a flexible tube, such as medical devices for inserting through a curved or tortuous path. For example, the teachings herein may be employed in a catheter, stent or an access sheath.

BACKGROUND

Examples of medical devices for inserting into a curved path are described in U.S. Pat. No. 8,721,826 B2, and PCT Patent Applications WO2014074986 A1 and WO2010105649 A1, all incorporated herein by reference. In general, these devices employ a tubular material that flexes back and forth. To enhance the flexing, the tubular structure may have slits or openings that reduce the resistance to the bending motion. However, at the bend points or bend regions, the tube is a contiguous material, directly connected and the ability to bend the tubular material requires that it be formed of a generally flexible material.

There is a need for tubular members which can be turned on one or more directions to fit through a curved or tortuous path. There is a need for tubular members having adjacent components that are easily rocked against each other. There is also a need for tubular members that are porous. There is also a need for tubular members that are kink free and/or kink resistant. There is also a need for tubular members that can easily move in an axial direction in response to an axial force (e.g., for moving in and out of a curved or tortuous path).

SUMMARY

In one aspect, the teachings herein are directed at a medical device comprising: a tubular member having a proximal end, a distal end, an outer surface, an inner surface, a longitudinal direction (i.e., an axial direction) along a length of the tubular member, a passage extending from the proximal end to the distal end in the longitudinal direction, and a cross-section perpendicular to the longitudinal direction. The tubular member includes a plurality of axial support components in a stacked arrangement including at least a first axial support component and a second adjacent axial support component located above the first axial support component in the proximal direction, wherein each of the first and second axial support components has a top edge surface facing the proximal end and a bottom edge surface facing the distal end, wherein a first portion of the top edge surface of the first axial support component contacts a first portion of the bottom edge surface of the second axial support component (e.g., so that an axial force is translated between the adjacent axial support components), and a second portion of the top edge surface of the first axial support component is spaced apart from the bottom edge surface of the second axial support component (e.g., so that the axial direction can bend between adjacent axial support components), wherein the first and second portions of the top edge surface are at different locations along the circumference of the first axial component. The tubular member also includes one or more lateral support components in contact with the axial support components for reducing lateral movement of adjacent axial support components relative to each other.

In another aspect, the teachings herein are directed at the manufacture of a device including a plurality of axial support components and one or more lateral support components.

In another aspect, the teachings herein are directed at a method comprising inserting a device into a cavity or other opening and steering an end of the device through the opening.

BRIEF DESCRIPTION OF DRAWINGS

FIG. 4 is a front view of an illustrative tubular member including a plurality of axial support members (e.g., in a stacked arrangement) and having an internal passage with one or more components extending through the internal passage.

FIG. 5 is a perspective view illustrating features that may be found in a tubular member.

FIG. 20 shows the top view, FIG. 21 shows the front view, and FIG. 22 shows the left side view.

FIG. 23A is a drawing of a front view of an illustrative arrangement of axial support components.

FIG. 23B is a drawing of a front view of an illustrative first axial support component of FIG. 23A.

FIG. 23C is a drawing of a front view of an illustrative second axial support component of FIG. 23A having a different shape as the first axial support component or arranged at an angle of rotation (e.g., about 180°) relative to the first axial support component.

FIG. 24A is a drawing of a front view of an illustrative arrangement of axial support components.

FIG. 24B is a drawing of a front view of an illustrative first axial support component of FIG. 24A.

FIG. 24C is a drawing of a front view of an illustrative second axial support component of FIG. 24A having a different shape as the first axial support component or arranged at an angle of rotation (e.g., about 180°) relative to the first axial support component.

FIG. 25A is a drawing of a front view of an illustrative arrangement of axial support components.

FIG. 25B is a drawing of a front view of an illustrative first axial support component of FIG. 25A.

FIG. 25C is a drawing of a front view of an illustrative second axial support component of FIG. 25A having a different shape as the first axial support component or arranged at an angle of rotation (e.g., about 180°) relative to the first axial support component.

FIG. 25D is a drawing of a front view of an illustrative third axial support component of FIG. 25A having a different shape as the first and second axial support component and/or arranged at an angle of rotation (e.g., about +/−90°) relative to the first axial support component.

FIG. 25E is a drawing of a front view of an illustrative fourth axial support component of FIG. 25A having a different shape as the first, second, and third axial support components or arranged at an angle of rotation (e.g., about 180°) relative to the third axial support component.

DETAILED DESCRIPTION

Figure 1:
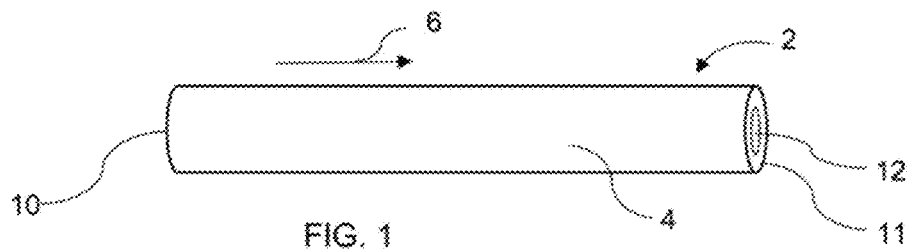
FIG. 1 is a perspective view of an illustrative tubular member having an internal passage in a generally linear configuration.

The devices, methods, and apparatus according to the teachings herein, provide a tubular member having a structure that can be easily inserted into a curved passageway and provides an at least partially contained passage within the tubular structure for inserting a functional component into the curved passageway. The tubular member employs a plurality of axial support components that are aligned along an axis (e.g., in the length direction) of the tubular member which are shaped to allow for a rocking motion between some or all of the adjacent axial support components. The structure of the tubular members provides for one or more (e.g., all of the following benefits): ease of bending of the tubular member, resistance of kinking and/or obstruction of the passage of the tubular member, or increased efficiency in transferring axial forces for the insertion of the tubular member into a curved passageway. With such properties, a structure preferably may either be actively manipulated, or passively adapted to the shape of a tortuous path as the structure is pushed through the path. The adjacent axial support components (e.g., adjacent along the length direction of the tubular member) are not directly connected at one or more positions of contact, so that the adjacent axial support components can rock in one or more directions (e.g., in a forward direction and/or in a backward direction) for the bending of the tubular member. A steering component may be employed for controlling the direction of bend of an end of the tubular member. When in a tilted state, adjacent axial support components preferably maintain two or more spaced apart regions or points of contact, so that transfer of axial forces is improved.

A stacked arrangement of short rigid cylindrical tubes each having a length and each having the same uniform cross-section may be employed in a bendable tube. However, when adjacent cylindrical tubes are bent relative to one another, there will only be a single point of contact between the two components. Such an arrangement will make it difficult to apply an axial force for translational motion in the axial direction, as this force will be focused at the single contact point.

By employing axial support components having a multiple contact points when tilted, it may be easier to apply a force necessary to insert the tubular member into a passage.

Tubular Member

The tubular member has a passage (e.g., a primary passage) extending from a first end (e.g., a proximal end) to a second end (e.g. a distal end). The tubular member includes a plurality of components (e.g., axial support components and lateral support components) that allow the tubular member to bend while maintaining a continuous passage from the first end to the second end. It will be appreciated that the passage through the tubular member has an axial direction that may be curvilinear and capable of changing to conform to the shape of a passage (e.g., a body passage) through which the tubular member is inserted. The tubular member has an inner surface facing the passage of the tubular member and an opposing outer surface. The components of the tubular member may be arranged so that the axial direction of the passage is generally linear and the tubular member has an initial length in the axial direction. When the passage of the tubular member is in a curved configuration, the length of passage is generally maintained at about the initial length.

The cross-section of the tubular member perpendicular to the axial direction of the passage may have any shape. For example, the cross-section may have a generally circular shape, a generally elliptical shape, a generally oval shape, a generally lens shape, a generally arch shape, a generally egg shape, or a generally polygonal shape. Preferably, the tubular member has a cross-section having a circular shape, an elliptical shape or an oval shape. Most preferably, the tubular member has a cross-section having a circular shape.

It will be appreciated that the tubular member generally has a proximal end, a distal end, an outer surface, an inner surface, an axial direction along a length of the tubular member, a passage extending from the proximal end to the distal end in the axial direction, and a cross-section perpendicular to the axial direction.

Axial Support Components

Each tubular member includes a plurality of axial support components. Each axial support component includes a passage extending the length of the axial support component. The passages of the axial support components are aligned for forming at least a portion of the passage of the tubular member. Each axial support component includes one or more walls in the direction of the passage for transferring a force in the axial direction from one axial support component to an adjacent axial support component. The one or more walls of the axial support component generally extend around a circumference of the axial support component. However, the walls of some or all of the axial support component do not completely surround the passage. Instead, as discussed herein, some or all of the axial support components includes a cut-out region or other opening formed between two adjacent axial support components, so that the axial support components can rock back and forth relative to each other. As such, the axial direction (e.g., of a passage) of an axial support component may tilt relative to the axial direction of an adjacent axial support component. This rocking/tilting motion of the axial support components allows them to pass through an opening that is not straight.

The rocking or tilting motion of two adjacent axial support components occurs at one or more regions or points of contact between the adjacent axial support components. At least one of the axial support components has a rocking portion (e.g. a lobe region) where the outer surface of the axial support component is convex. One of the axial support components may have a generally flat surface in the region of contact so that the rocking motion is defined by the rocking of the convex surface against a generally planar surface. Alternatively, both axial support components may have a convex surface in the region of contact. It will be appreciated that in addition to one of the axial support components having a generally convex shape in the rocking portion, the two axial support components may have a mating structure that assists in the alignment of the two components. For example, the axial support components may have mating gears, mating groove and channel. Preferably, any such mating structure does not interfere with the rocking movement between the two axial support components.

A pair of adjacent axial support components includes two spaced apart regions where contact is maintained as they tilt or rock against each other. The multiple spaced apart contacts between adjacent axial support components increases the ability to translate axial forces and/or axial motion between the adjacent axial support components (e.g., and along the length of the tubular member). The ability for adjacent axial support components to freely rock may allow for the use of generally rigid materials, as there is no need for the material of the axial support component to bend. In contrast, it is desirable for the axial support component to be generally stiff and resist bending or other deformation.

Due to the rocking motion, adjacent axial support component may be able to tilt to a higher angle than in a tubular member where the tilting is restricted to the bending of the material. As such, the tubular member according to the teachings herein may allow for bending at a low radius and/or allow for tubular members having a large diameter (or a larger cross-sectional area).

Figure 18:
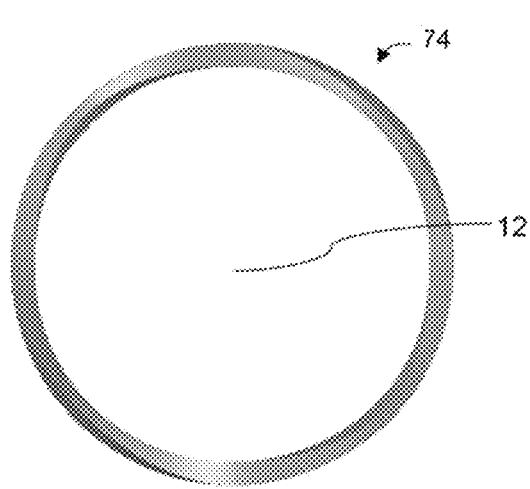
FIG. 18 is a top view of FIG. 16A, showing the passageway through the structure.
Figure 19:
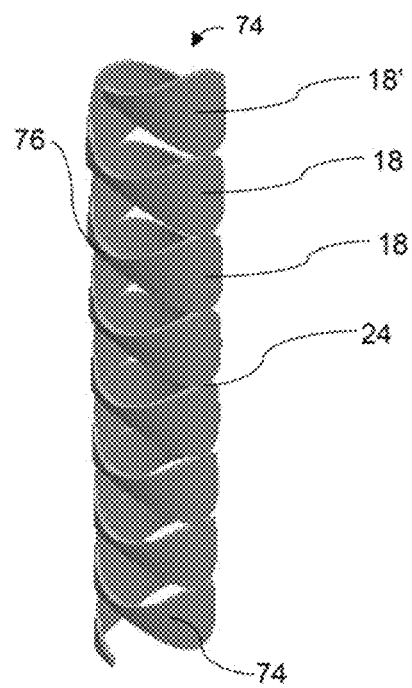
FIG. 19 is a representative side view of FIG. 16A showing the helical structure.
Figure 20:
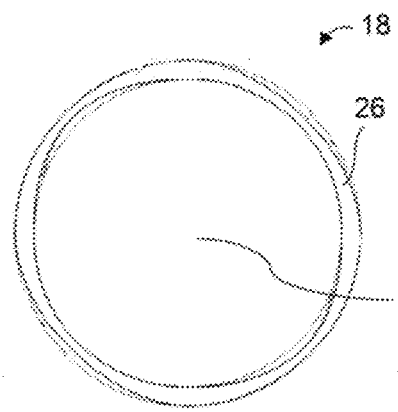
FIG. 20, FIG. 21, and FIG. 22 are views of an illustrative axial support component as represented by a single turn of the helical structure of FIG. 16A.
Figure 21:
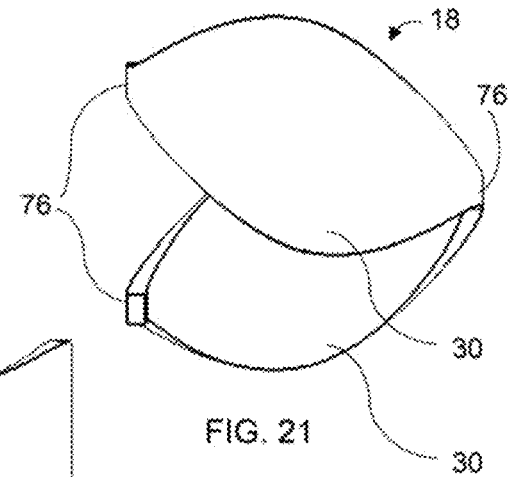
Figure 22:
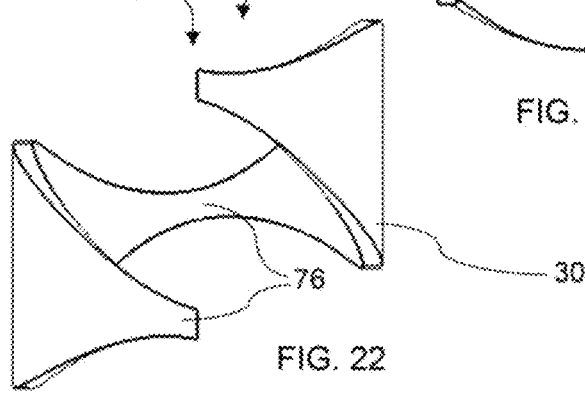
Figure 26:
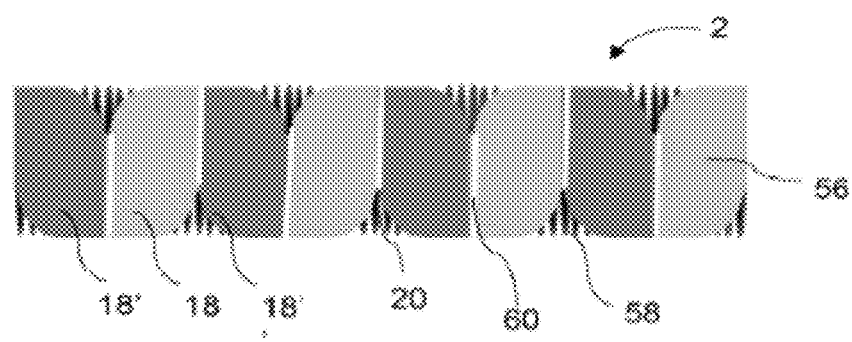
FIG. 26 is a drawing of a front view of a tubular member showing stacked axial support components having adjacent axial support components connected by a corrugated region.
Figure 27:
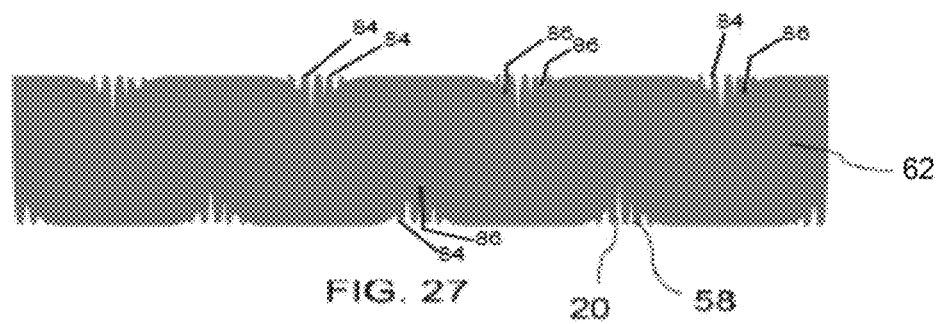
FIG. 27 is a drawing of an illustrative precursor part for preparing the structure of FIG. 26. In the precursor part, the adjacent axial support components may be directly attached, and the manufacturing process may include making a cut between adjacent axial support components.
Figure 28:
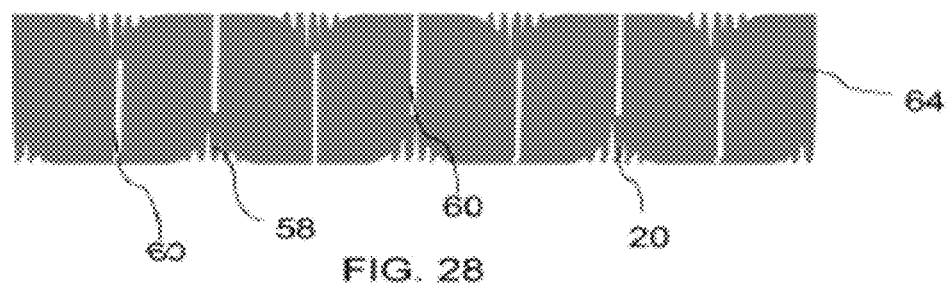
FIG. 28 is a drawing of the structure of FIG. 27 having a plurality of cuts each between a pair of adjacent axial support components.
Figure 29:
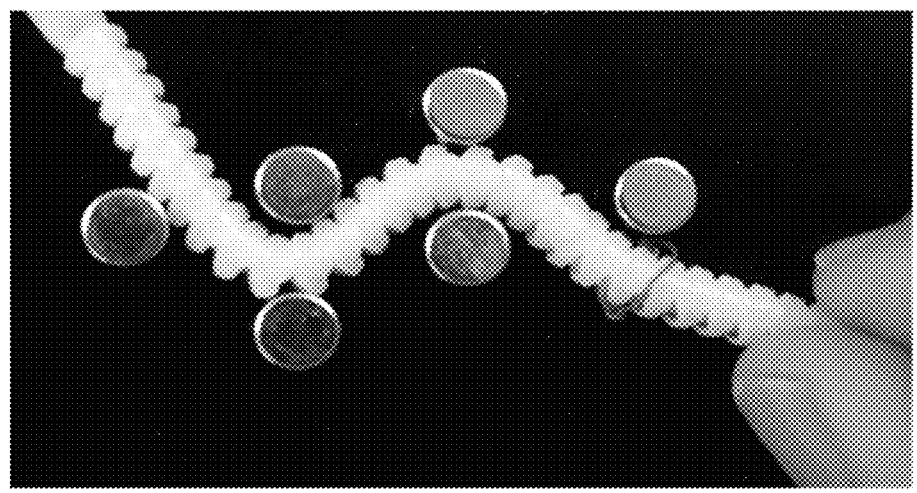
FIG. 29 is a side view of a tubular member according to the teachings herein being pushed through a tortuous path.

An axial support component may generally have a ring shape. The ring shape may be a closed ring (such that there is a continuous path about the circumference of the axial support component. A tubular member including axial support components having a closed ring shape is seen for example in FIG. 5. The ring shape may be an open ring, having a first circumferential end and a second circumferential end. For example, the first end and the second circumferential end may be separated in the axial direction. An example of an open ring is a helical structure, such as illustrated in FIGS. 21 and 22. The ring shape, may be most easily seen when viewing an axial support component from the top, such as shown in FIGS. 18 and 20 for an open ring and FIG. 12 for a tubular member having axial support components with a closed ring shape. The ring shape preferably has a shape that increases the ease of inserting the tubular member into a passage or other opening. For example, the ring shape may be free of sharp corners. Most preferably the ring shape is a circular shape, an oval shape, an egg shape, an elliptical shape, or other shape having only curved or rounded corners.

Preferably, some or all of the axial support components include two spaced apart rocking regions which are connected by one or more lateral connectors. The spaced apart rocking regions may be lobed regions. The rocking regions are preferably spaced apart along the circumference of the axial support component. For example, the rocking regions may be spaced apart by an angle of about 120° to about 240°, and most preferably about 180° (i.e., 180°+/−20°, +/−10°, or +/−5° as defined by the angle from the axis in the center of the passage of axial support component to the two rocking regions as projected onto a plane perpendicular to the axis.

It will be appreciated that a pair of spaced apart rocking regions may cooperate to tilt the axial support component relative to an adjacent axial support component. The cooperation between the two spaced apart rocking regions may be enhanced by a lateral connector. In the case of a closed ring, the rocking regions may be connected along opposing sides (e.g., a first lateral connector along a right side and a second lateral connector along a left side). In the case of an open ring structure, such as a helical ring structure, a rocking region may be connected to spaced apart rocking region using a first lateral connector, and preferably to a second spaced apart rocking region using a second lateral connector. One or more of the lateral connectors in an axial support component may have a height (in the length direction of the axial support component) that is less than the height the axial support component in the rocking region so that an opening or cut out region is formed that allows the two axial support components to approach each other as they are tilted and rocked. A lateral connector preferably has a sufficient thickness and height so that the spacing between the two rocking regions is generally maintained.

The rocking region (e.g., lobe region) of the axial support component and the lateral connector of the axial support component may be formed of materials that are the same or different. Preferably, the rocking region and the lateral connector are formed of the same material. More preferably, an entire ring structure of the axial support component or even an entire axial support component is a monolithic structure, and most preferably formed of a single material.

An axial support component may be made of a material sufficiently rigid so that axial forces can be transferred along the length of the tubular member. The axial support component may be formed of one or more metals, one or more polymers, or one or more ceramics, one or more reinforcing fillers, or any combination thereof. Preferably, the axial support component is formed of a material including one or more polymers. For example, the axial support component may be formed of a polymeric material having a flexural modulus of about 100 MPa or more, about 250 MPa or more, about 600 MPa or more, or about 1500 MPa or more, or about 2000 MPa or more. Unless otherwise specified, the flexural modulus may be measured according to ASTM D790B. Typically, polymeric materials have a flex modulus of about 8000 MPa or less, or about 4000 MPa or less.

The axial support component may have an axis of rotation (e.g., the axial direction of a passageway extending the length of the axial support component). The axial support component typically is not symmetrical about the axis of rotation.

Each axial support component has an opening at each end for forming at least a portion of the passage of the tubular member. The alignment of the axial support components allows for the continuous, generally unobstructed passage of the tubular member through the axial support components. In addition to the openings at the ends, an axial support component may have openings along the sides for the flow of a fluid into and/or out of the passage. Such side openings may allow for the equilibration of a pressure within and outside of the passage or for removal of a liquid through the tubular member. It may be desirable for a section of the tubular member to have side openings and for a section of the tubular member to be generally free of such side opening.

Two adjacent axial support components generally are configured so that they may tilt relative to each other. The tilting preferably is in a single plane. The tilting of a second axial support component relative to a first axial support component may be in one direction (e.g., a forward direction or a backward direction) or may be in two directions (e.g., both a forward direction and a backward direction). When tilted, the two adjacent axial support components remain in contact at two or more spaced apart positions.

A first axial support component may have a first axial end and an opposing second axial end. The first axial support component may be arranged between a second axial support component and a third axial support component. The first axial end of the first axial support component may contact the second axial support component and the second axial end of the first axial support component may contact the third axial support component. The second axial support component may be capable of tilting in a first angular direction (i.e., about a first tilt axis) relative to the first axial support component and the third axial support component may be capable of tilting in a second angular direction (i.e., about a second tilt axis) relative to the first axial support component that is the same or different from the first direction. For example, the first tilt axis may be parallel to the second tilt axis or may be angled. By way of example, the first tilt axis may be perpendicular to the second tilt axis so that the second axial support component tilts forward and/or backward relative to the first axial support component and the third axial support component tilts left and/or right relative to the first axial support component. As such, the tubular member may tilt along multiple planes so that it can readily conform to the shape of a passage that is non-planar.

The cross sectional shape of the axial support component is not uniform along the length of the axial support unit (i.e., in the axial direction).

The adjacent support components may tilt about a tilt axis defined by a line connecting two spaced apart contact points. An axial support component may have a region proximate to a second axial support component where the two axial support components tilt about a tilt axis.

The axial support components may be arranged in a generally helical shape. For example, a single turn of the helical shape may define an axial support component having one or more (e.g., two or three or more) and preferably two contact regions with an adjacent axial support component. The tilting of the adjacent axial support components may be accomplished by the cooperative rocking at two spaced apart contact regions. As the contact regions may be offset along the length direction, it will be appreciated that the tilt axis may be angled relative to the planes normal to the length direction of each of the axial support components. At each contact region, at least one of the axial support components has a generally convex outer surface for rocking against a surface of the adjacent axial support component. Two spaced apart rocking regions may be connected by a lateral connector. For example, two spaced apart rocking regions of a first axial support component may be connected by a first lateral connector and a rocking region of the first axial support component may be connected to a rocking region of an adjacent axial support component by a second lateral connector.

The tubular member may have a large number of axial support components so that the tubular member can bend along a tortuous path. The number of axial support components in the tubular member preferably is about 10 or more, more preferably about 20 or more, even more preferably about 40 or more and most preferably about 60 or more.

The tubular members may be assembled by stacking discrete axial support components. It may be beneficial to reduce the number of different parts to be assembled. As such, two or more of the axial support components may have the same shape or be identical. Most, substantially all of, or all of the axial support components may be selected from a small group of 4 or less different shaped components (or even 2 or less different shape components. For example, 20% or more, 50% or more, or 80% or more of the axial support components may generally have the same shape or be identical.

Preferably, the stack of axial support components includes one or any combination of the following features: (i) two adjacent axial support components that generally have the same shape or are identical; (ii) two axial support components, separated by a single axial support component, that are generally have the same shape or are identical; or two axial support components, separated by exactly three axial support components, that generally have the same shape or are identical.

Although two axial support components may have the same shape or be identical, it will be appreciated that the two components may be aligned in various configurations. For example, the two axial support components may be rotated (e.g., at about 45 degrees, 90 degrees, 135 degrees, or 180 degrees) about the axial direction of the tubular member. As another example, the two axial support components may be inverted relative to one another. As another example, they two axial support components may be both rotated and inverted.

A pair of adjacent axial support components may be capable of tilting by an angle of (i.e., may have a maximum tilt angle of) about 3° or more, about 7° or more, about 15° or more, about 28° or more, about 36° or more or about 44° or more. The maximum tilt angle may be about 70° or less, about 55° or less, or about 45° or less. The maximum tilt angle between a first and an adjacent second axial support component may be the maximum acute angle between the axial direction of the passages in the two adjacent axial support components.

Axial support components may be arranged in a spiral configuration. For example, the axial support component may be in the form of an open ring. One or more ends of an open ring may be connected with an end of another axial support component. For example, all of the axial support components may be connected to form a long spiral. The axial support component may have a periodicity, $L_p$. Along the circumference of the spiral, there may be contact regions where the axial support component has a length (i.e., in the axial direction), $L_c$, about equal to the periodicity, $L_p$, so that adjacent spirals can contact in these regions. Between the contact regions, there are regions where the length of the axial support component is reduced, so that the adjacent axial support components can tilt (i.e., rock). The regions of reduced length may be referred to as cut-out regions. Every ring, or every turn of the spiral, preferably has 2 or more, 3 or more, or 4 or more contact regions. For example, if there are 2 contact regions (e.g., at about 90° and at about 270° angles about the spiral) per turn of the spiral, the tubular member may be able to tilt back and forth (e.g., in the direction of about 0° and about 180° angle about the spiral). As another example, if there are 4 contact regions per turn of the spiral, the tubular member may be able to tilt back and forth and also tilt left and right. It will be appreciated that intermediate tilt directions can be achieved by tilting in multiple directions. As such, it may be possible to use the tubular member to navigate a passage that is curved or tortuous in three dimensions.

The axial support components may be formed of a single material or from two or more materials (e.g., to form a composite structure or a reinforced structure). By way of example, the axial support component may include one or more metal materials, one or more polymer materials, or one or more ceramic materials. The axial support component may include one or more filler reinforcements, such as a particulate reinforcement or a fiber reinforcement. The selection of the material for the axial support components may be the result of manufacturing or cost considerations. For example, in a polymer fabrication process (e.g., a molding, an extrusion or a blow molding process), the material may include a polymer composition selected for ease of use in the fabrication process. As another example, in a 3D manufacturing process, the material may include one or more material employed in the art of 3D manufacturing. The material for the axial support components should be selected so that an axial force for the insertion of the tubular member into a passageway can be partially or entirely translated from axial support component to axial support component along the length of the tubular member.

Lateral Support Components

The tubular member includes one or more lateral support components. A lateral support component preferably functions to reduce, minimize or eliminate lateral movement between adjacent axial support components and/or to reduce, minimize, or eliminate axial separation between adjacent axial support components. Preferred lateral support components are in contact with or connected with two adjacent axial support components. For example, a lateral support component may reduce or eliminate lateral movement of adjacent axial support components relative to each other (except for the rocking or tilting motion as described herein). Preferably, there is a lateral support component for each adjacent pair of axial support components.

Preferably, the lateral support components allow for the adjacent axial support components to rock relative to each other. As such, the lateral support components should be formed of a material or include one or more features that allow the axial direction of the passage through a first axial support component to be tilted relative to the axial direction of the passage through an adjacent axial support component. For example, the lateral support component may have a lower wall thickness, may include hinge features (e.g., one or more crests or valleys and/or one or more ridges or roots, such as in a bellows), may have an axial length that is relatively low (e.g., the ratio of the axial length of a lateral support component to the axial length of an axial support component may be about 0.7 or less, about 0.5 or less, about 0.35 or less, or about 0.20 or less, may be formed of a material having a lower flexural modulus relative to the material of the axial support component, or any combination thereof.

Although, the axial support components and the lateral support components may be made of the same materials or may be made of different materials, in one approach the lateral support component preferably is made of a material that is different from the axial support component or is shaped to allow for the rocking motion of adjacent axial support components. As one example, the lateral support component may be a support layer (such as a cylindrical layer or other tubular layer) over the outside surface of the axial support components and/or a support layer within the inside surface of the axial support components. Such a support layer may be sufficiently flexible and/or sufficiently thin so it can bend (e.g., with the rocking movement of the axial support components) without kinking or obstructing the passage through the tubular member. A support layer preferably extends at least the length of the axial support components, and may even extend about the entire length of the tubular member. A support layer preferably is provided as a tubular shaped sheet, a fabric layer, or a combination thereof. The support layer preferably contacts the axial support components or is separated by the axial support components by a nominal gap distance (e.g., a gap distance of about 0.5 mm or less, about 0.2 mm or less, about 0.1 mm or less, or about 0.03 mm or less). The support layer may be attached to one or more (or even all of the axial support components). However, if a support layer is attached to a plurality of axial support components, it preferably is attached at a location and/or in a manner that does not prohibit the rocking motion between adjacent axial support components. For example, the support layer may be attached near a lateral connector region. Preferred support layers are formed of a polymeric material. The polymeric material may be a monolithic material. The polymeric material may be a woven or nonwoven fabric. Preferred polymeric materials include one or more amorphous polymers (e.g., having a glass transition temperature above a use temperature, so that the polymer is substantially below its glass transition temperature at one or more use temperatures), one or more semi-crystalline polymers (e.g., having a final melting temperature above a use temperature, so that the semi-crystalline polymer has at least some crystalline structure at the use temperature), or a combination thereof. Preferred semi-crystalline polymers have a final melting temperature. of about 40° C. or more, about 60° C. or more, or about 80° C. or more, as measured by differential scanning calorimetry. The semi-crystalline polymer may have a final melting temperature of about 360° C. or less, about 200° C. or less, or about 150° C. or less, as measured by differential scanning calorimetry. The semi-crystalline polymer preferably has a crystallinity of about 1 percent or more, more preferably about 4 percent or more, and most preferably about 9 percent or more, as measured by differential scanning calorimetry. The semi-crystalline polymer preferably has a crystallinity of about 50 percent or less, more preferably about 40 percent or less, even more preferably about 30 percent or less, and most preferably about 25 percent or less. The lateral support component may include or be made from a fabric. Preferred fabrics are stretchable. Stretchable fabrics may be made from a material and or woven so that the fabric can be stretched. Preferably, the stretchable fabric has an elongation in one or more directions of about 5% or more, about 10% or more, about 20% or more, about 30% or more, or about 50% or more (as measured according to ASTM D3107-07 after 30 minutes at a tension of 3 pounds). The stretch fabric preferably includes, consists substantially of (e.g., includes 80% or more, 90% or more, or 95% or more), or consists entirely of one or more elastic yarns. For example, the stretch fabric may recover some (about 50% or more, about 75% or more, about 90% or more, or about 95% or more) or all of its stretched portion upon removal of the tension. The lateral support component may be formed of a material having a lower hardness (e.g., as measured according to ASTM D 2240 in units of Shore A durometer or Shore D durometer) than a material employed in the axial support component. Preferably, the difference in the Shore A durometer of the material of the axial support component less the Shore A durometer of the material of the lateral support component is about 5 or more, about 10 or more, about 15 or more, or about 25 or more (in Shore A units).

As another example, a lateral support component may be connected to each of two adjacent axial support components and include one or more hinges that allows for the rocking motion between the axial support components. Such a lateral support component may even be formed of the same material as the axial support components. For example, the lateral support component may have a bellows shape (e.g., having a cross-section with one or more ridges and one or more valleys). Such a lateral support component may span the space between lateral connectors of the adjacent axial support components, such as described herein. For example, as the lateral connectors rock towards each other, the bellows may become compressed, so that the distance between the valleys become decreased. When the lateral connectors rock away from each other, the bellows may become expanded, so that the distance between the valleys is increased.

A lateral support component may seal off some or all of the openings in the axial support components. For example, the tubular member may only have openings at the ends of the passage. It will be appreciated that the lateral support component may have openings which allow for the flow of a fluid into the passage through a side of the tubular member.

A surface of the tubular member (e.g., an outer surface or an inner surface of the tubular member) may be hydrophilic and/or lubricious. Such a characteristic may be obtained by the selection of material for a component of the tubular member (e.g., an axial support component or a lateral support component), by treating a surface of the tubular member, or by an additional layer or component.

The tubular member may include one or more control components for steering a leading end of the tubular member. For example, the tubular member may include one or more cables connected to the leading end to be steered. By applying a tension to a cable, the direction of tilt of a leading end may be controlled. The tubular member may include one or more eyelets or other spaced apart along the length of the tubular member for managing the position of the cables in the passage of the tubular member. For example, the tubular member may include eyelets protruding from the axial support components (e.g., in the region of the lateral connectors) into the passage of the tubular member. Preferably the tubular member includes two or more spaced apart control cables.

The tubular member may include one or more covers, such as a cover over the axial support components. The cover may provide a protection to the axial support component or a protection a passageway from damage by the axial support component. The cover, if employed, may provide a functional feature for an intended application.

The tubular member may include a lumen, such as a central lumen. If employed the lumen may be porous or non-porous.

The tubular member according to the teachings herein is preferably employed in an application requiring the insertion of the tubular member into a curved passage and/or requiring the steering of the leading end of the tubular member.

The device may include a functional component in the passage of the tubular member or may be adapted for receiving a functional component in the passage. It will be appreciated that the device may be supplied as a kit including both the functional component and the device including the tubular member. The functional component may be a component for one or any combination of the following: delivering an item for a medical procedure, viewing a medical procedure, removing an item from a medical procedure, positioning a medical component within or adjacent to an organ or body part, attaching a medical component to an organ or body part, making a surgical incision, and repairing an organ or body part.

The tubular member according to the teachings herein may be employed in a medical application. For example, the tubular member may be employed for a stent, an access catheter, an access cannula or an access sheath. The tubular member may be employed as an utereral access sheath, such as for access to a bladder or a kidney. The tubular member may be employed for the removal of a stone or stone fragment, such as the hydraulic removal of a stone or stone fragment. The tubular member may be employed during lithotripsy, such as an intrarenal lithotripsy.

Process of Manufacture

The components and or tubular members according to the teachings herein may be manufactured by any known process. For example, a component may be manufactured using a process including molding (e.g., injection molding or compression molding), casting, extrusion, blow molding, co-injection molding, insert molding, or any combination thereof, layered printing (i.e., 3D printing), machining (such as cutting, milling, drilling), or any combination thereof.

Two or more axial support components may be manufactured as an attached multi-component structure or may be manufactured as individual units. The process may include a step of stacking two or more individual units or stacking two or more multi-component structures. It will be appreciated that all of the axial support components may be manufactured as a single multi-component structure (e.g., in a stacked arrangement) so that there is no need for stacking of the axial support components. The manufacturing process may include one or both of the following steps: slicing or otherwise separating two or more axial support components (e.g., in a contact region and/or rocking region), cutting out one or more openings (e.g., to form a cut-out region, such as between two lateral connectors). Such step(s) may be of particular use when the axial support components are manufactured as a single multi-component structure.

A molding process may be employed for manufacturing an axial support component. A lateral support component may optionally also be molded (e.g., from the same material, or preferably from a different material, such as a material having a lower flexural modulus). A preferred molding is an injection molding process, such as a polymer injection molding process. If the process includes molding the axial support component(s) and the lateral support component(s) from different material, the process may employ a co-injection molding process or an overmolding process, for sequentially forming the two components.

The axial support components may be formed by an extrusion process, such as a polymer extrusion process. For example, a polymeric tube may be extruded and then processed so that the cut-out regions are formed, the rocking regions are formed, and at least the contact regions are separated so that the adjacent axial support components can rock in one or more directions. It will be appreciated that the extrusion process may include extruding one or more layers. For example, a functional surface layer may be co-extruded with a structural layer.

The axial support components may be formed using a blow molding process, such as a polymer blow molding process. Such a process may be particularly useful for simultaneously forming a structure for multiple axial support component and for multiple lateral support components. For example, the blow molding process may produce sections having ridges and valleys (e.g., for the lateral support components) with other sections that suitable for forming the axial support components.

The axial support components may be formed by a layered printing process or other 3D printing process. Such a process may employ a polymeric material, a ceramic material, a particulate material, a binder material, a metallic material, or any combination thereof. The layered or other 3D printing process may be employed for producing individual axial support components or for producing a stacked arrangement of a plurality of axial support components. It will be appreciated that a layered or other 3D printing process may also be employed for simultaneously printing a lateral support component (using the same or different material).

EXAMPLES

Figure 2:
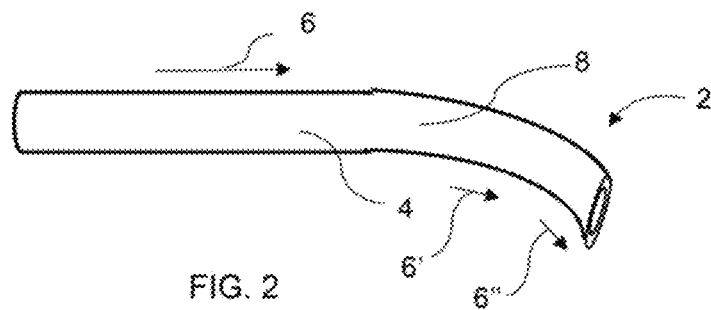
FIG. 2 is a perspective view of an illustrative tubular member having an internal passage and having a non-linear (e.g., curved) configuration.

A tubular member 2 may be capable of being arranged in a generally straight configuration, such as illustrated by FIG. 1. The tubular member 2 has an axial direction 6, which is generally uniform when the tubular member is in a straight configuration. The tubular member has an outer surface 4. The outer surface 4 may cover the entire length and circumference of the tubular member, or the tubular member may have openings, cut-outs, or other passages along the length of the tubular member. The tubular member has a first end 10 and an opposing second end 11, and a passage extending the length of the tubular member from the first end to the second end. The tubular member 2 may also be arranged in a curved configuration 8, so that at least a portion of its length is generally curved, such as illustrated in FIG. 2. With reference to FIG. 2, the axial direction 6, 6', 6" may vary along the length of the tubular member 2. For example, the tubular member may include one or more regions having a generally uniform or constant axial direction 6, and/or one or more regions having an axial direction that varies along the length of the tubular member.

Figure 3:
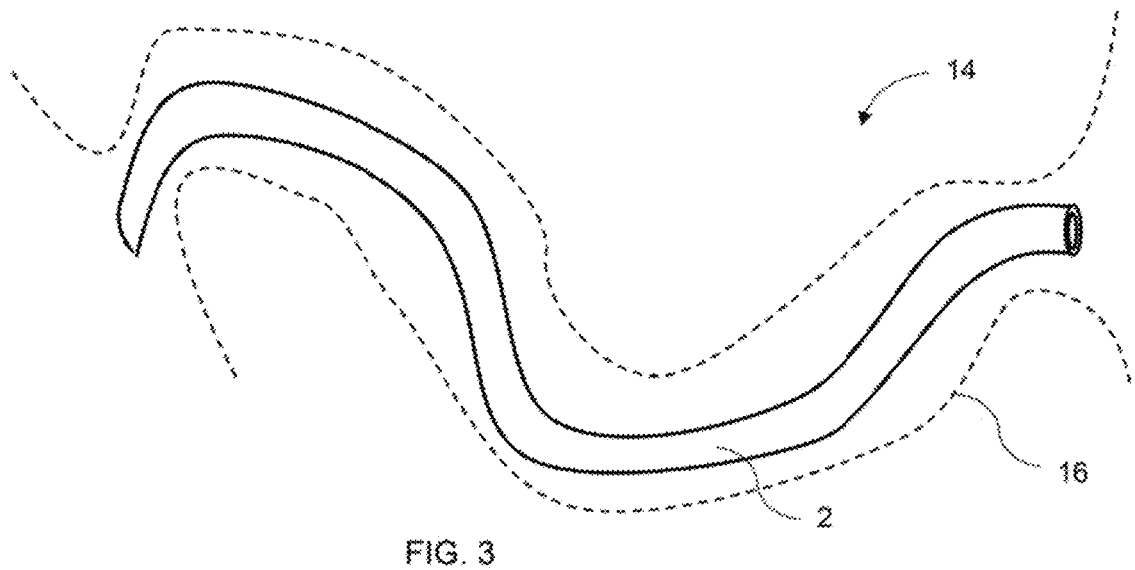
FIG. 3 is a perspective view of an illustrative tubular member in a tortuous passage.

The tubular member 2 preferably is steerable so that it can be inserted into a curved or even a tortuous passage, such as illustrated in FIG. 3. As the tubular member 2 is inserted into the curved or tortuous passage, a leading end of the tubular member may be steered along the boundary and/or walls 16 of the passage.

FIG. 4 is a side view showing features of a device including a tubular member 2 according to the teachings herein, and having a functional component 22 extending through the passage 12 of the tubular member 2. The tubular member includes a plurality of axial support components 18, 18'. Adjacent tubular members may be different, or may have substantially identical shapes, such as illustrated in FIG. 4. The adjacent axial support components (e.g., 18, 18') contact at multiple spaced apart contact points (e.g., two contact points). Axial forces required for inserting a tubular member into a passage may be transferred between adjacent axial support members through the contact points. The tubular member 2 also includes one or more lateral support components 20. The lateral support components may provide lateral stability to the tubular member 2, so that adjacent axial support components generally remain aligned for providing a sufficient and continuous passage 12 for the functional components 22 to pass through. The one or more lateral support components may include or consist essentially of one or more support sheaths, such as a tubular sheath inserted inside the passage formed by the axial support components and/or a tubular sheath positioned outside the axial support components. Such a support sheath preferably is capable of flexing without kinking, so that axial support components can tilt relative to each other without obstructing or blocking the passage of the tubular component. A support sheath preferably contacts a surface of the axial support components or is within a narrow gap (e.g., about 1 mm or less, about 0.2 mm or less, about 0.1 mm or less, or about 0.05 mm or less) of the axial support components for defining the lateral alignment of the axial support components.

FIG. 5 is a perspective view showing a portion of the tubular member of FIG. 4. With reference to FIG. 5, the axial support components 18, 18' have a structure that allow adjacent axial support components to tilt in one or more directions. The axial support components may have a first edge surface (e.g., a top edge surface) 26 and an opposing second edge surface (e.g., a bottom edge surface) 28. The top edge surface of one axial support component 18 may face the bottom edge surface 28 of an adjacent axial support component 18'. Adjacent axial support components (e.g., 18 and 18', or 18 and 18") may contact at two spaced apart contact regions or contact points 24. One or both of the adjacent axial support components may have a lobe region(s) 30 that includes the contact region or contact points 24. For example, as illustrated in FIG. 5, both adjacent axial support components may have lobe regions that meet at two spaced apart contact points 24 (only one of the two contact points between 18 and 18' is visible in FIG. 5). The axial support component may include regions 25 that do not contact an adjacent axial support component. The tubular member may include cut-out regions 32 between adjacent axial support components. It will be appreciated that a cut-out region 32 may be formed by cutting out material or may be a structure defined by the shape and arrangement of adjacent axial support components. The tubular member may have one or more rigid regions 33, where the tubular member generally does not bend. Preferably any rigid regions are positioned at one of the ends 10, 11, and most preferably at the second end 11 (e.g., an end that will not be inserted into a curved passage). The device may include one or more control components (e.g., guide wires) 34 for steering or otherwise controlling a tilt of the tubular component. The tubular member may have a cover layer or support sheath 36 (shown as a transparent layer). The features shown in FIG. 5 are further illustrated in FIG. 6 (front view) and FIG. 7 (side view).

Figure 6:
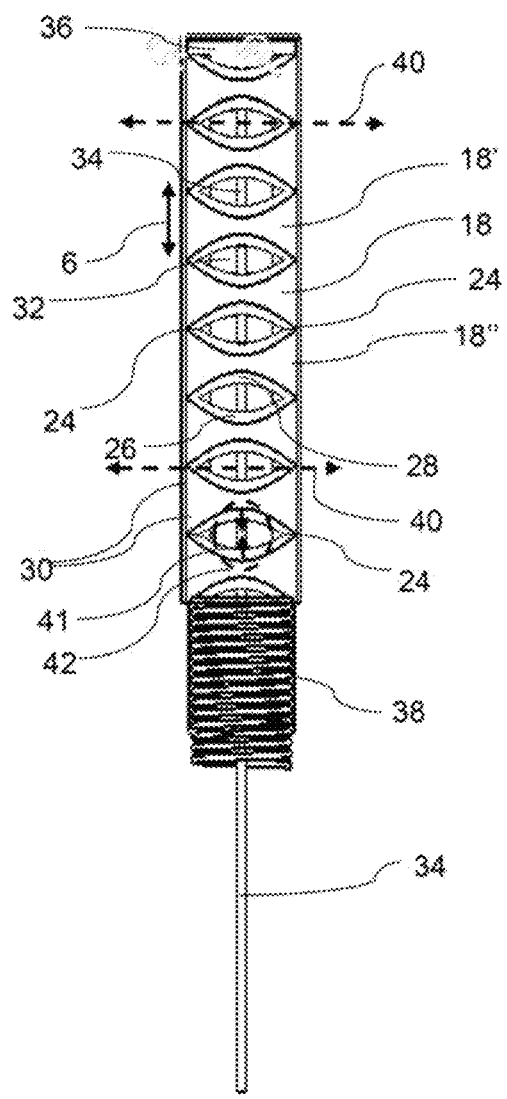
FIG. 6 is a front view of FIG. 5.
Figure 7:
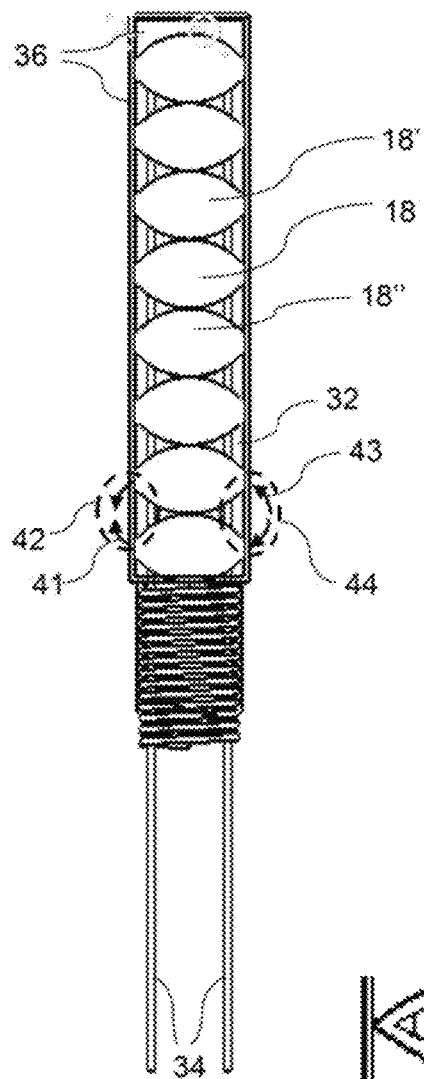
FIG. 7 is a right side view of FIG. 5.
Figure 8:
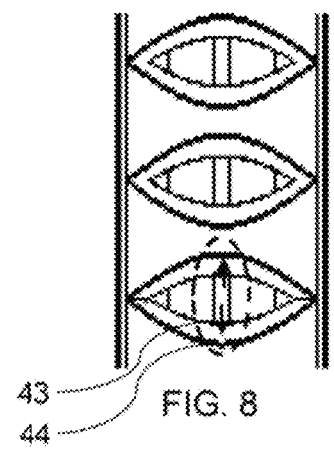
FIG. 8 is a rear view of a portion of FIG. 5.

With reference to FIG. 6, the adjacent axial support components 18, 18', 18" may tilt about a tilt axis 40. When two adjacent axial support components tilt in the forward direction about the tilt axis 40, their facing edge surfaces 26, 28 in the front cut-out region 32 may move together in a contracting direction 41 with the cut-out region 32 decreasing in size. As shown in FIG. 7, a first portion 42 of the adjacent axial support components move together (e.g., in a contracting direction 41) and a second portion 44 of the adjacent axial support components move apart (e.g., in an expanding direction 43). During the tilt of the adjacent axial support components, two points or regions of contact 24 are maintained. It will be appreciated that the axial components in FIGS. 5, 6, and 7 can also tilt in a reverse or backward direction due to the mirror symmetry (about a plane defined by the axial direction and the tilt axis) of each axial support components. The tubular member may have an end region 38 that is generally rigid. For example, the end region 38 may have a structure that reduces, minimizes, or prevents bending. As illustrated in FIG. 6 and FIG. 7, the end region 38 may be a generally solid tubular region (e.g., without cut-outs, slits, or other openings). The end region 38 may include one or more structures for attaching the tubular member 2 to other components. For example, the end region 38 may be threaded, such as shown in FIG. 6 and FIG. 7. FIG. 8 is an enlarged view of a region of FIG. 6.

Figure 9:
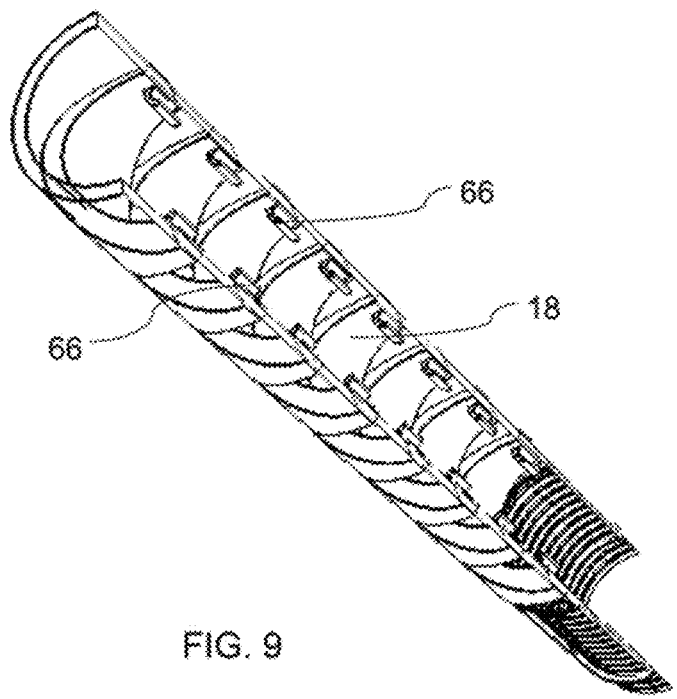
FIG. 9 is a perspective view sectioned by a plane going through the axis of the passage, showing features of the tubular member of FIG. 5.
Figure 10:
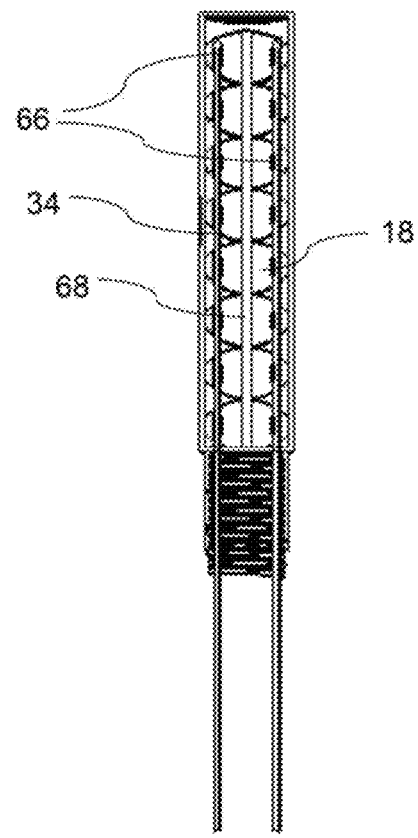
FIG. 10 is a left side view sectioned by a plane through the axis of the passage showing features of the tubular member of FIG. 5.
Figure 11:
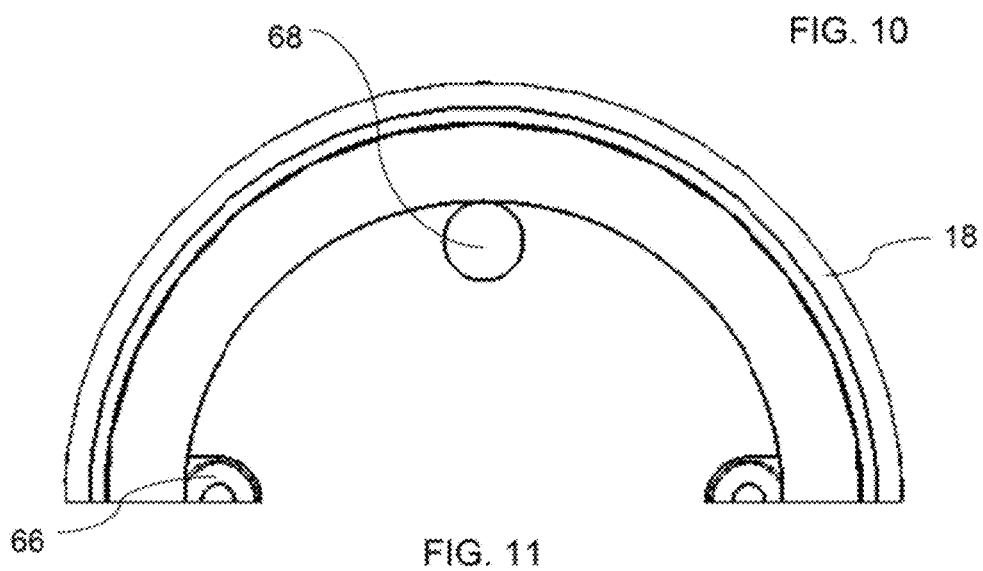
FIG. 11 is a top view showing features of the tubular member of FIG. 10.

Some or all of the axial support components may include an eyelet 66 or other component for supporting the control component 34 (not shown), such as illustrated in FIG. 9. Preferably, tubular member includes a sufficient number of eyelets or other components for positioning one or more (preferably two or more) control components in the passage of the tubular member. For example, one or more (preferably each) of the axial support components may have a pair of spaced apart eyelets for positioning two spaced apart guide wires. With reference to FIG. 10, the control components 34 may be threaded through the eyelets 66. The tubular member may have one or more tethers 68, such as illustrated in FIG. 11.

Figure 12:
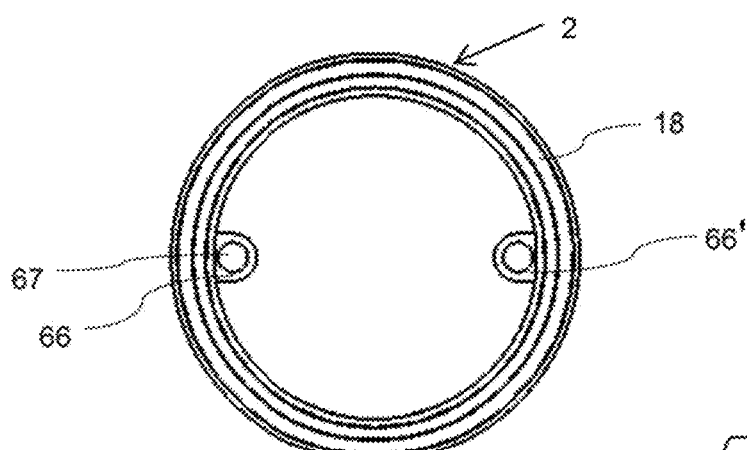
FIG. 12 is a top view of an illustrative tubular member according to the teachings herein.

Preferably the tubular member 2 includes a first set of eyelets 66 and a second set of eyelets 66' which are spaced apart (e.g., by about 180°), such as illustrated in FIG. 12. The eyelets may include an opening for 67 for threading a control component through. It will be appreciated that the tubular member may include additional sets of eyelets for controlling a tilt of the end of the tubular member in more than two directions. By way of example, the tubular member may include three or more sets of eyelets (e.g., three sets of eyelets spaced apart by about 120°, or four sets of eyelets spaced apart by 90°). Two sets of eyelets may allow for the steering of an end of the tubular member in a single direction (e.g., in a forward and backward direction). Two sets of eyelets arranged at a 90° angle may allow for the independent steering of the tubular member in two orthogonal directions (e.g., in a front or back direction and in a right or left direction). It will be appreciated that additional steering of the tubular member may be facilitated by rotating the tubular member.

Figure 13:
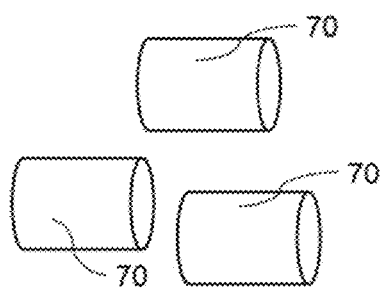
FIG. 13 is a perspective view of components that having top and bottom edges that mate with one another.
Figure 14:
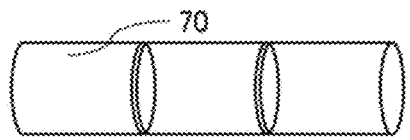
FIG. 14 is an illustrative drawing showing the components of FIG. 13 stacked in an axial direction.
Figure 15:
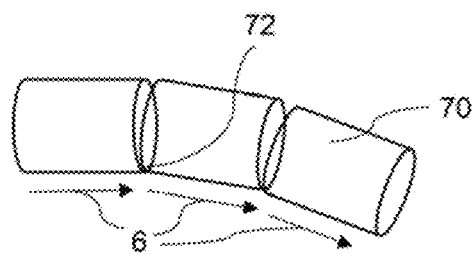
FIG. 15 is an illustrative drawing showing the components of FIG. 13 stacked with each component angled relative to an adjacent component.

As discussed herein, when adjacent axial support components are tilted, they preferably maintain two spaced apart contact points or contact regions. However, such multiple contacts is not typically achieved if the axial support components are regular cylindrical tubes 70, such as illustrated in FIG. 13. These axial support components 70 may be arranged in a stacked arrangement, such as illustrated in FIG. 14. As the cylinders have the same dimensions and mate together, complete contact between the facing surfaces is achieved when the tubular member is in a linear arrangement. However, when the tubular member is bent, such as illustrated in FIG. 15, there is only a single point or region of contact between adjacent axial support components 70. When in this bent or tilted arrangement with a single point of contact, it may be difficult to effectively transfer axial forces along a series of stacked axial support components.

Figure 16A:
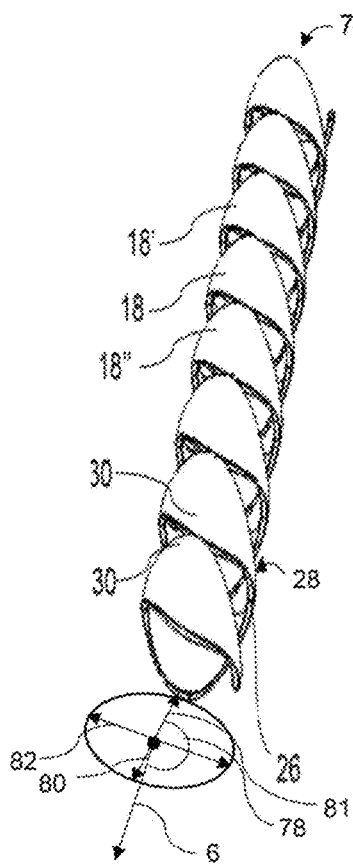
FIG. 16A is a perspective view showing features of an illustrative axial support component having a generally helical structure.
Figure 16B:
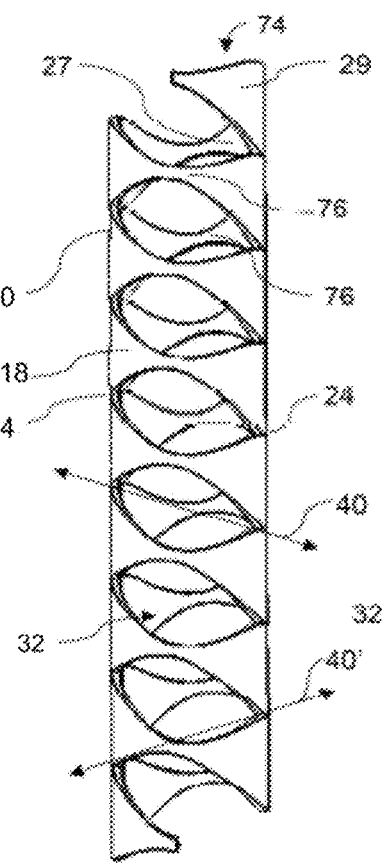
FIG. 16B is a front view showing the arrangement of the axial support components of FIG. 16A.
Figure 16C:
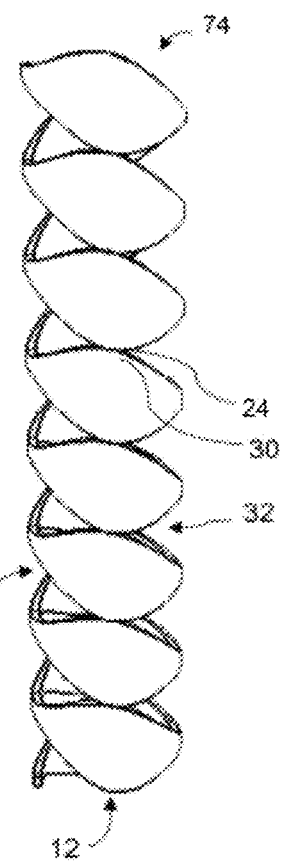
FIG. 16C is a left side view of FIG. 16A.
Figure 17A:
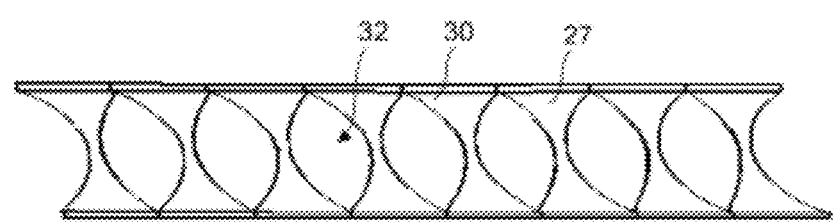
FIG. 17A is a sectional view of FIG. 16B.
Figure 17B:
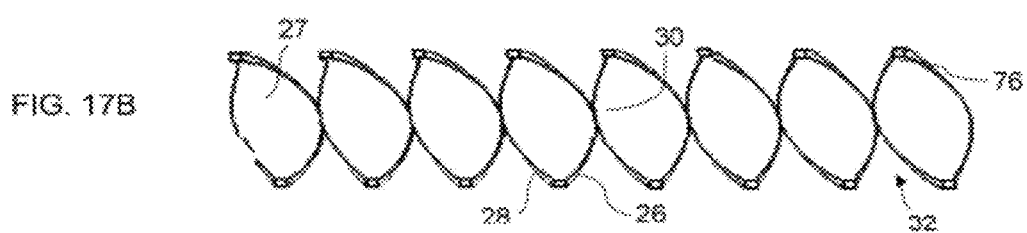
FIG. 17B is a sectional view of FIG. 16C.

The axial support components may be arranged in a helical structure, such as illustrated in FIG. 16A, FIG. 16B, and FIG. 16C, showing a structure that includes a plurality of axial support components having the open ring structure illustrated in FIGS. 20, 21, and 22. Preferably, an axial support component is represented by a single turn of the helix. Each turn of the helix preferably includes two or more lobe regions (e.g., where the axial support component can rock or tilt against an adjacent axial support component). Although an axial support component may include three or more spaced apart lobe regions, it preferably has two lobe regions for contacting one of the adjacent axial support components at two contact regions (for example spaced apart at an angle of about 180°). A first lobe region 30 may be connected to another lobe region 30 of the axial support component via a lateral connector 76. The first lobe region 30 may also be connected to a lobe region of an adjacent axial support component by another lateral connector 76, such as illustrated in FIG. 16B. Although the axial support components may have lateral connectors 76, the adjacent axial support components are not directly connected at the contact points or contact regions 24. It will be appreciated that when the axial support components tilt, they may tilt about different tilt axis when tilting in a generally forward direction compared to when tilting in a generally rearward direction. As illustrated in FIG. 16B, the tilt axis for tilting in a forward direction 40 may be angled relative to the tilt axis for tilting in a generally rearward direction 40'. With reference to FIG. 16C and FIG. 17B, an axial support component may include a lobe region 30 for rocking or tilting against a lower axial support component and/or a lobe region 30 for rocking or tilting against a high axial support component. The axial support components provide a generally unobstructed passage 12 at least partially surrounded by the walls of the axial support components, such as illustrated in FIG. 18. In the case of the helical arrangement, the rocking or tilting is provided by the cooperative tilting at two contact points or contact regions that are also spaced apart in the length direction. For example, the two contact points or contact regions 24 may be spaced apart by a fraction turn (e.g., a half turn) of the helix, such as shown in FIG. 16B.

Two axial support components may have facing surfaces that include a first portion that mates with (e.g, the first portion may be coplanar) and a second portion that is separated, such as illustrated in FIG. 23A. The facing surfaces of the two axial support components may have a contact area that is generally large (e.g, about 2 percent or more, about 5 percent or more, about 10 percent or more, or about 15 percent or more, based on the total area of the facing surface) when the two axial support components are in a "rest state", such as a generally aligned state (e.g., when their axial directions are aligned). In such an aligned state, the ratio of the contact area to the total area of the facing surface is typically about 90 percent or less, about 70 percent or less, about 60 percent or less, or about 55 percent or less. When the two axial support components are rocked (i.e., tilted) so that their axial directions are angled with respect to one another, the contact between the axial support component decreases and is typically about 5 percent or less, about 3 percent or less, about 2 percent or less, or about 1 percent or less of the total area of the facing surface. In such a tilted arrangement, the contact may be limited to two regions or points of contact that are spaced apart. The two regions or points of contact preferably are spaced apart by an angle (i.e.

a spread angle) of about 60 degrees or more, more preferably about 90 degrees or more, even more preferably about 120 degrees or more, and most preferably about 150 degrees or more, as measured from the axis of the passage of the axial support component. It will be appreciated that the spread angle between the spaced apart contact regions may change with the degree of tilt. For example, in some applications it may be desired for the spread angle between the spaced apart contact regions may increase and then decrease as the tilt between the two axial support components increases. In other applications, the axial support components may be configured so that the spread angle between the spaced apart contact regions continuously decrease as the tilt between the two axial support components increases.

It will be appreciated that rocker portion (e.g., a lobe region) of an axial support component may rock against a generally flat portion of an adjacent axial support component (such as shown in FIG. 23A) or against a generally curved portion, such as a lobe region, of an adjacent support component (such as shown in FIG. 24A).

REFERENCE NUMBERS

2 Tubular member
4 Outer surface of the tubular member
6 Axial direction/axis of the tubular member
8 Curved configuration of tubular member
10 First end
11 Second end
12 Passage extending the length of the tubular member
14 Tubular member in a tortuous passage
16 Boundary and/or wall of the tortuous passage
18, 18', 18", 18'" Axial support component
19 Passage extending the length of an axial support component
20 Lateral support component
22 Functional component
24 Contact regions (e.g., contact points) of two adjacent axial support components
25 Regions of axial support component (e.g., top or bottom edge surface) that do not contact another axial support component.
26 Top surface (e.g., top edge surface) of the axial support component
27 Inside surface of axial support component
28 Bottom surface (e.g., bottom edge surface) of the axial support component
29 Outside surface of axial support component
30 Rocking region or rocker portion (e.g., lobe region) of axial support component
32 Cut-out region of axial support component
34 Control components (e.g., for steering the tubular member, such as guide wire or guide line)
36 Cover layer
38 End region
40 Tilt axis
41 Direction of movement between two axial adjacent support components (e.g., on a front or rear)
42 Portions of adjacent axial support regions moving together (e.g. cut-out region decreasing in size)
43 Direction of movement between two axial support components (e.g., on the opposite of the front or rear of 41)
44 Portions of adjacent axial support regions moving apart (e.g., cut-out region increasing in size)
46 Axial support components arranged for tilting in a first direction
47 Axial support components arranged for tilting in a second direction
48 Axial support components arranged for tilting in a third direction
49 Axial support components arranged for tilting in a fourth direction
50 Curved region of an edge surface (e.g., top edge or bottom edge)
52 Flat surface region (e.g., horizontal) of an edge surface (e.g., top edge or bottom edge)
54 Axial support components in a stacked arrangement
56 Tubular member including corrugated region
58 Corrugated region having flutes or other structure having alternate ridges and grooves.
60 Space or cut between adjacent axial support components
62 Tubular member precursor (e.g., attached axial support components)
64 Tubular member with axial support components unattached from adjacent axial support components.
66 Eyelet or other component for supporting the control component
67 Opening for receiving a control component
68 Tether
70 Cylinders having uniform cross-section (along the length)
72 Single point of contact
74 Helical shaped tubular member
76 Lateral connectors
78 Angular spacing between two lobe regions (i.e., angle between 80 and 81)
80 Direction between axis of the passage and a first lobe region
81 Direction between axis of the passage and a second lobe region
82 Direction between axis of the passage and a lateral connector
84 Ridge
86 Valley

What is claimed is:

1. A medical device comprising:
a tubular member having a proximal end, a distal end, an outer surface, an inner surface, a longitudinal direction along a length of the tubular member, a passage extending from the proximal end to the distal end extending along the longitudinal direction, and a cross-section perpendicular to the longitudinal direction;
wherein the tubular member includes
  i) a plurality of helical axial support components in a stacked arrangement including at least a first axial support component and a second axial support component located adjacent to and above the first axial support component in the distal direction, wherein each of the plurality of helical axial support components has a top edge surface facing the proximal end and a bottom edge surface facing the distal end,
  the top edge surface of the first axial support component has a first portion, a second portion, a third portion, and a fourth portion in sequential order around a circumference of the top edge surface of the first axial support component,
  the bottom edge surface of the second axial support component has a corresponding first portion, a corresponding second portion, a corresponding third portion, and a corresponding fourth portion in sequential order around a circumference of the bottom edge surface of the second axial support component, wherein the first and third portions of the top edge surface of the first axial support component contacts the corresponding first and third portions of the bottom edge surface of the second axial support component so that an axial force is translated between the adjacent first and second axial support components, and the second and fourth portions of the top edge surface of the first axial support component are spaced apart from the corresponding second and fourth portions of the bottom edge surface of the second axial support component so that the axial direction can bend between the adjacent first and second axial support components; and ii) one or more lateral support components in contact with the plurality of helical axial support components for reducing lateral movement between adjacent pairs of the plurality of helical axial support components.

2. The device of claim 1, wherein the first axial support component and the second axial support component have the same shape.

3. The device of claim 1, wherein the one or more lateral support components includes a central lumen having a passage therethrough for defining at least a portion of the inner surface of the tubular member.

4. The device of claim 1, wherein the number of the plurality of axial support components is about 10 or more.

5. The device of claim 4, wherein the one or more lateral support components includes a lateral support component connected to both the first and second axial support components.

6. The device of claim 5, wherein the plurality of axial support components and the one or more lateral support components are formed of the same material.

7. The device of claim 4, wherein the plurality of axial support components are formed of a first material and the one or more lateral support components are formed of a second material, wherein the first and second materials are different materials.

8. The device of claim 7, wherein the second material has a Shore A durometer less than a Shore A durometer of the first material.

9. The device of claim 7, wherein the second material is a stretchable fabric.

10. The device of claim 4, wherein the adjacent first and second axial support components are not directly attached at a point of contact between the opposing edge surfaces.

11. The device of claim 10, wherein the first axial support component rocks back and forth in a first direction relative to the second axial support component.

12. The device of claim 4, wherein the first axial support component includes structural features for stiffening the first axial support component.

13. The device of claim 4, wherein the tubular member has a porous wall.

14. The device of claim 4, wherein the outer surface of the tubular member is coated with a hydrophilic coating.

15. The device of claim 1, wherein the device includes one or more control components extending the length of the tubular member for controlling a direction of bend of the proximal end of the tubular member.

16. A medical device comprising:

a tubular member having a proximal end, a distal end, an outer surface, an inner surface, a longitudinal direction along a length of the tubular member, a passage extending from the proximal end to the distal end extending along the longitudinal direction, and a cross-section perpendicular to the longitudinal direction;

wherein the tubular member includes, in an unbent configuration:

i) a plurality of helical axial support components in a stacked arrangement including at least a first axial support component and a second axial support component located adjacent to and above the first axial support component in the distal direction, wherein each of the plurality of helical axial support components has a top edge surface facing the proximal end and a bottom edge surface facing the distal end, wherein a first portion of the top edge surface of the first axial support component contacts a corresponding first portion of the bottom edge surface of the second axial support component so that an axial force is translated between the adjacent first and second axial support components, and a second portion of the top edge surface of the first axial support component is spaced apart from a corresponding second portion of the bottom edge surface of the second axial support component so that the axial direction can bend between the adjacent first and second axial support components, wherein the first and second portions of the top edge surface of the first axial support component are at different locations along the circumference of the first axial support component; and ii) one or more lateral support components in contact with the plurality of helical axial support components for reducing lateral movement between adjacent pairs of the plurality of helical axial support components;

iii) wherein the tubular member, starting in the unbent configuration, is capable of tilting in different directions, including a forward direction and a backward direction.

17. The device of claim 16, wherein when the tubular member is in a bent state, the first axial support component has two or more spaced apart contacts with the second axial support component.

* * * * *

UNITED STATES PATENT AND TRADEMARK OFFICE
CERTIFICATE OF CORRECTION

PATENT NO. : 10,441,748 B2  
APPLICATION NO. : 15/155697  
DATED : October 15, 2019  
INVENTOR(S) : Fan et al.

Page 1 of 1

It is certified that error appears in the above-identified patent and that said Letters Patent is hereby corrected as shown below:

On the Title Page

In item (71), in "Applicant", in Column 1, Line 1, after "INC.,", insert --d/b/a Olympus Surgical Technologies America,--

In item (73), in "Assignee", in Column 1, Line 1, after "INC.,", insert --d/b/a Olympus Surgical Technologies America,--

In the Claims

In Column 18, Line 50, In Claim 1, after "includes", insert --:--

Signed and Sealed this  
Sixteenth Day of February, 2021

Drew Hirshfeld  
*Performing the Functions and Duties of the*  
*Under Secretary of Commerce for Intellectual Property and*  
*Director of the United States Patent and Trademark Office*